(12) United States Patent
Busson et al.

(10) Patent No.: US 6,271,431 B1
(45) Date of Patent: Aug. 7, 2001

(54) PROCESS FOR THERMAL PYROLYSIS OF A FEEDSTOCK THAT CONTAINS ETHANE

(75) Inventors: Christian Busson, Charbonniere; Jean-Pierre Burzynski, Sainte-Foy-les Lyon; Henri Delhomme; Luc Nougier, both of Sainte-Foy-les Lyons, all of (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/454,999

(22) Filed: Dec. 6, 1999

(30) Foreign Application Priority Data

Dec. 4, 1998 (FR) .................................................. 98 15359

(51) Int. Cl.⁷ .............................. C07C 4/02; C10G 9/36
(52) U.S. Cl. .......................... 585/652; 585/648; 585/650; 585/921; 208/130
(58) Field of Search .................................... 585/648, 650, 585/652, 921; 208/130

(56) References Cited

U.S. PATENT DOCUMENTS

| | | | |
|---|---|---|---|
| 4,777,318 | * 10/1988 | Martens et al. ...................... | 585/613 |
| 5,300,216 | * 4/1994 | Hertzberg et al. ................... | 208/130 |
| 5,554,347 | * 9/1996 | Busson et al. ....................... | 422/204 |
| 5,990,370 | * 11/1999 | Sims .................................... | 585/650 |

FOREIGN PATENT DOCUMENTS 0 666 104   8/1995  (EP) .

* cited by examiner

Primary Examiner—Walter D. Griffin
Assistant Examiner—Tam M. Nguyen
(74) Attorney, Agent, or Firm—Millen, White, Zelano & Branigan, P.C.

(57) ABSTRACT

A process for thermal pyrolysis of a feedstock containing at least 80% ethane to convert to ethylene at a conversion rate of at least equal 80% by feeding the feedstock into a reaction zone in which heating means are arranged approximately perpendicular to the direction of flow of the feedstock. The temperature of the outlet of the heating zone in the reaction zone is between 880 and 960° C. and the dwell time of the feedstock in the heating zone is between 1005 and 3000 milliseconds.

14 Claims, No Drawings

PROCESS FOR THERMAL PYROLYSIS OF A FEEDSTOCK THAT CONTAINS ETHANE

The invention relates to a process for thermal pyrolysis of a feedstock that contains at least 80% ethane. The ethylene that is obtained is used in particular for the synthesis of polyethylene.

Ethylene is currently produced by steam-cracking the ethane, which is a process that is broadly described in the literature. Taking into consideration the limitations of the mechanical behavior, in terms of temperature, of the metallic materials that are currently used, the conversion of the ethane is less than 70%. There is therefore at least 30% of ethane that is recycled and that represents a significant cost because this ethane is to be compressed, cooled and separated from the effluent.

A recent so-called radiant-tube technology in ceramic furnaces that is described by the applicant (EP-B-542597, EP-B-666104) makes it possible to obtain an effluent with a high conversion of the feedstock, for example up to 100% if it is desired. Whereby the recycling of the unconverted feedstock is greatly reduced and even almost zero, it is possible either to reduce the size and therefore the cost of the separation section for the new installations or to increase productivity of olefins with the same separation section for an existing unit. Thus, according to the patent of the applicant EP-B-542597, the pyrolysis of the naphtha in a furnace that comprises electric resistors that are insulated from direct contact with hydrocarbons by porous sheaths that contain a gas is described, and an effluent with an ethylene yield by weight of 39.6% and 16.4% of propylene is produced.

According to another patent of the applicant, EP-B-664104, a reactor with pyrolysis by heat exchange means, at least some of which contain at least one tube that is formed by at least one jacket that is connected to a gas supply means or heat exchange gas mixture, is described. These heat exchange means that are fed by gas communicate with gas burners. The process that is employed describes the pyrolysis of a butane-isobutane mixture that is diluted in nitrogen and that makes it possible to obtain 9 mol % of a mixture of ethylene and acetylene that contains 37 mol % of acetylene.

To increase the selectivity toward the production of olefins, several previous studies quickly led to a very high-temperature heating of the furnaces and to decreasing the dwell time of the feedstock in the reaction zone. Unlike the teaching of these patents, it was noted that by operating at the lowest possible reaction temperature and with the longest possible dwell time in the reaction zone, it was possible to increase the conversion of the feedstock while keeping the ethylene selectivity at a very correct level, for example greater than 75%. None of these cited patents teach or suggest pyrolyzing an ethane feedstock in the presence of water vapor with long dwell times, greater than 1 second. This is therefore one of the objects of the invention.

Another object is to produce ethylene with a minimum of impurities and in particular acetylene. Another object is to produce ethylene with the highest selectivity possible for a given ethane conversion rate and more particularly in the range of high conversion levels.

More particularly, the invention relates to a process for thermal pyrolysis of a feedstock that contains at least 80% ethane by weight in a reaction zone that comprises a heating zone and a cooling zone behind the heating zone, characterized in that the operation is performed in the presence of water vapor under the following conditions:

temperature at the outlet of the heating zone of between 880° C. and 960° C., dwell time of the feedstock in the heating zone of between 1005 milliseconds and 3000 milliseconds (ms), in particular greater than 1020 milliseconds;

whereby the temperature and the dwell time are selected so that the conversion that is obtained of the feedstock is at least equal to 80%, and an effluent that contains ethylene for the most part is recovered.

It is preferably possible to proceed at a temperature at the outlet of the heating zone of between 890° C. and 950° C., most often between 910° C. and 930° C. and with a dwell time of the feedstock of 1050 milliseconds to 2800 milliseconds, most often 1200 milliseconds to 2000 milliseconds to convert at least 85% of the feedstock and most often at least 88%.

It was observed more particularly that it was possible to proceed at the lowest possible reaction temperature and with the longest possible dwell time of the feedstock in the heating zone that are compatible with the desired conversion rate.

Under these conditions, the recycling rates of unconverted feedstock in the pyrolysis reactor are reduced by operating under conditions that make it possible to convert the feedstock as much as possible, and the size of the equipment that is downstream from the separation is reduced since the ethylene selectivity is maximized. The process is therefore more economical.

The conversion reaction of the ethane according to the invention into ethylene can be implemented in a reactor in which the heating zone comprises heating means that are placed approximately perpendicular to the direction of the flow of the feedstock and the effluent.

This heating zone can comprise electric resistors that are encased in ceramic sheaths that are approximately perpendicular to the flow. The latter can contain at least one cover gas that can be water vapor or nitrogen. In patent EP-B 542597 that is incorporated as a reference, the applicant described an embodiment of the reactor that can be used for the implementation of the invention. According to a variant, the heating zone can comprise, as it is described in the patent of the applicant EP-B-666104 that is incorporated as a reference, a number of heat exchange means that are approximately perpendicular to the flow and that each comprise a tube that is formed by at least one jacket that is connected to a supply means of gas or a heat exchange gas mixture that is suitable for exchanging heat with the feedstock and/or the effluent that circulates outside of said heat exchange means a n d that comprises at least one evacuation means outside of the reactor of said gas or gas mixture that has exchanged heat with the feedstock and/or the effluent.

The feedstock, after having been preheated between 700° C. and 750° C., for example, can be heated in an increasing manner, for example an approximately linear manner, to the temperature that is selected at the end of the heating reactor.

According to a characteristic of the invention, it is possible to heat the heating zone according to a temperature gradient that is generally between 40° C./s and 350° C./s and preferably between 80° C./s and 150° C./s. As has been indicated, this gradient can be kept approximately constant during the heating period or even increases as a function of time. The heating zone preferably contains a number of rows in which the feedstock circulates and that comprise the heating elements that are perpendicular to them. These rows are separated by partitions that make it possible to increase the exchange surface. The form of these partitions can conform in shape to that of the heating elements. In a horizontal plane, each row preferably contains a single heating element between two adjacent partitions. An embodiment is described in Patent EP-B-666104 that is incorporated as a reference according to FIG. 1B of this patent.

Another embodiment of the reactor is described in the patent of the applicant EP-A-781828 that is incorporated as a reference, in which at least one row can be dedicated to a decoking stage by the water vapor during t he operation of the unit under endothermic conditions at a temperature that is compatible with that of the process according to the invention, while at least one row is intended for the steam-cracking of the feedstock.

The dwell time that is generally selected, the longest possible that is compatible with the lowest temperature of the isoconversion reactor, is linked to the reaction volume. To obtain it, for a given production of ethylene, it is possible to increase distance d between the heating element and the partition that separates two rows in a d/D ratio that is generally between 0.05 and 1, whereby D is the diameter of the heating element (sheath) that is compatible with the thermal flow that is provided by each heating element.

According to a characteristic of the process, a direct quenching, an indirect quenching or an indirect quenching followed by a direct quenching of the effluent is generally produced in the cooling zone behind the heating zone by a coolant that is known to one skilled in the art. The effluent can be cooled to a temperature of about 500° C., for example, and then collected.

The hydrocarbon feedstock that can be used within the scope of this invention is a feedstock that contains at least 80% ethane, advantageous at least 90% and most often at least 95%. The impurities contain ethylene for the most part and aliphatic hydrocarbons with 3 carbon atoms.

The ethane can come from a source of natural gas or refinery gases. It can result from thermal cracking or hydro-cracking of hydrocarbons and carbon liquefaction.

The hydrocarbon feedstock is generally preheated to a temperature of 600 to 750° C. before its introduction into the pyrolysis reactor.

The water vapor can be introduced into this reactor according to a flow ratio of 0.2:1 to 2.0:1 relative to that of the feedstock.

EXAMPLE

A horizontal reactor with direct quenching, whose heating means consist of electric resistors of silicon carbide of the Crusilite type of the KANTHAL Company, is used. These resistors are encased in sintered silicon carbide sheaths that are placed concentrically relative to the center of the circle that includes the resistors.

These sheaths, of which there are 16 in a single row, are placed in a line that is perpendicular to the direction of circulation of the feedstock (vertically). The length of each resistor is 100 mm and its diameter 10 mm. The ceramic sheaths have a length of 110 mm, an outside diameter of 50 mm and an inside diameter of 42 mm. The distance that separates two adjacent sheaths or one sheath and the wall of the reactor of refractory concrete is 5 mm.

The temperature of the gas along the reactor is regulated thermally by thermocouples that are placed in the spaces where the feedstock circulates. At the outlet of the reactor, the effluent is cooled by direct contact with nitrogen at 500° C., and it is then cooled in an exchanger at ambient temperature.

The feedstock that is preheated to 750° C. is heated in an approximately linear manner with a thermal gradient of 115° C./second to the temperature that is selected at the end of the reactor. The dwell time is selected by varying the feedstock flow rate.

Thus, for a dwell time of 400 ms, the feedstock flow rate will be on the order of 3.65 m$^3$/h TPN and for 1500 ms on the order of 1.05 m$^3$/h. The operating pressure is 1.5 bar absolute.

As a feedstock, ethane that contains 1% by weight of ethylene that is diluted in water in a ratio by weight of water vapor/ethane of 0.6 is used. The results are presented in the table below.

For each column, the numbers in the "conditions" line correspond for the first to the dwell time in ms and for the second to the temperature at the outlet of the heating reactor of C°.

The selectivity is defined relative to the number of carbons of product P to the number of carbons of the transformed feedstock, multiplied by 100.

| Test No. | 1 | 2 | 3 | 4 | 5 | 6 | 7 |
| --- | --- | --- | --- | --- | --- | --- | --- |
| Conditions | 2800/ 850 | 2800/ 890 | 1500/ 910 | 1050/ 920 | 800/ 930 | 400/ 940 | 200/ 960 |
| Methane | 5.18 | 7.40 | 8.08 | 8.95 | 10.51 | 11.75 | 13.24 |
| Acetylene | 1.68 | 2.10 | 2.50 | 2.70 | 3.56 | 3.65 | 4.85 |
| Ethylene | 85.56 | 78.55 | 76.72 | 75.50 | 72.82 | 70.84 | 67.53 |
| Total C3 | 1.44 | 1.30 | 1.44 | 1.46 | 1.40 | 1.61 | 1.75 |
| Total C4 | 2.44 | 4.45 | 4.20 | 4.18 | 4.12 | 4.07 | 4.02 |
| Total C5 | 0.53 | 1.01 | 1.05 | 1.08 | 1.15 | 1.09 | 1.12 |
| Benzene | 1.15 | 3.20 | 3.96 | 4.12 | 4.49 | 4.90 | 5.20 |
| C7 + C8 | 0.30 | 0.82 | 0.69 | 0.60 | 0.53 | 0.45 | 0.40 |
| CO | 0.17 | 0.37 | 0.32 | 0.42 | 0.47 | 0.36 | 0.39 |
| CO2 | 0.37 | 0.14 | 0.16 | 0.15 | 0.12 | 0.14 | 0.15 |
| Coke | 0.18 | 0.68 | 0.87 | 0.84 | 0.82 | 1.12 | 1.35 |
| Conversion | 78.53 | 90.47 | 90.86 | 90.75 | 90.80 | 90.57 | 90.68 |

For Test No. 1, although the dwell time is long, it is seen that with a temperature at the outlet of the reactor of 850° C., the conversion is less than 80%.

Then, 6 tests were performed by selecting each time a temperature-dwell time pair that makes it possible to have a conversion on the order of 90–91%. For tests 2 to 4 with a dwell time that varies between 1050 and 2800 ms, a high ethylene selectivity (between 75.5 and 78.5%) is obtained, whereas for tests 5 to 7 with a dwell time that varies between 200 and 800 ms, the ethylene selectivity is clearly lower (between 67.5 and 72.8%).

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 98/15.359, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for thermal pyrolysis of a feedstock that contains at least 80% ethane in a reaction zone that comprises a heating zone in which heating means are arranged approximately perpendicular to the direction of flow of the feedstock and of the effluent that is produced and also comprises a cooling zone behind the heating zone, characterized in that the operation is performed in the presence of water vapor under the following conditions:

temperature at the outlet of the heating zone of between 880° C. and 960° C., dwell time of the feedstock in the heating zone of between 1005 and 3000 milliseconds;

whereby the temperature and the dwell time are selected so that the conversion that is obtained from the feedstock is at least equal to 80%;

and an effluent that contains ethylene for the most part is recovered.

2. A process according to claim 1, wherein the heating zone comprises a plurality of heat exchange means each comprising a tube formed by at least one jacket connected to a supply means of gas or a heat exchange gas mixture suitable for exchanging heat with the feedstock and/or the effluent that circulates outside of said heat exchange means and that comprises at least one means for evacuation outside of the reactor of said gas or gas mixture that has exchanged heat with the feedstock and/or the effluent.

3. A process according to claim 1, wherein the heating zone comprises electric resistors that are encased by ceramic sheaths.

4. A process according to claim 1, wherein the heating zone comprises heating means that are encased by sheaths that contain at least one cover gas that is selected from the group that is formed by water vapor and nitrogen.

5. A process according to claim 1, wherein the heating zone is heated according to a temperature gradient that is between 40° C./s and 350° C./s.

6. A process according to claim 1, wherein the heating zone is heated according to an approximately constant temperature gradient.

7. A process according to claim 1, wherein the operation is performed at a temperature at the outlet of the heating zone of between 890° C. and 950° C., and with a dwell time of the feedstock of 1050 milliseconds to 2800 milliseconds, to convert at least 85% of the feedstock.

8. A process according to claim 1, wherein the operation is performed at the lowest possible reaction temperature and for the longest possible dwell time of the feedstock in the reaction zone that are compatible with the desired conversion rate.

9. A process according to claim 1 to, wherein the water vapor is introduced at a flow ratio by weight of 0.2:1 to 2.0:1 relative to the feedstock.

10. A process according to claim 1 to, wherein in the cooling zone, a direct quenching, an indirect quenching or an indirect quenching followed by a direct quenching of the effluent is carried out.

11. A process according to claim 5, wherein the temperature gradient is between 80° C./s and 150° C./s.

12. A process according to claim 7, wherein the temperature at the outlet of the heating zone is between 910° C. and 930° C.

13. A process according to claim 7, wherein the dwell time is 1200 to 2000 milliseconds.

14. A process according to claim 7, wherein at least 88% of the feedstock is converted.

* * * * *